(12) United States Patent
Krumme et al.

(10) Patent No.: US 8,998,849 B2
(45) Date of Patent: Apr. 7, 2015

(54) MEDICAL INJECTOR AND ADAPTER FOR COUPLING A MEDICAMENT CONTAINER AND AN ACTUATOR

(75) Inventors: John Krumme, Woodside, CA (US); John Parissenti, Menlo Park, CA (US)

(73) Assignee: Nordson Corporation, Westlake, OH (US)

( * ) Notice: Subject to any disclaimer, the term of this patent is extended or adjusted under 35 U.S.C. 154(b) by 544 days.

(21) Appl. No.: 13/499,034

(22) PCT Filed: Oct. 7, 2010

(86) PCT No.: PCT/US2010/051800
§ 371 (c)(1),
(2), (4) Date: Jun. 14, 2012

(87) PCT Pub. No.: WO2011/044346
PCT Pub. Date: Apr. 14, 2011

(65) Prior Publication Data
US 2012/0265143 A1 Oct. 18, 2012

Related U.S. Application Data

(60) Provisional application No. 61/249,380, filed on Oct. 7, 2009.

(51) Int. Cl.
*A61M 37/00* (2006.01)
*A61M 1/00* (2006.01)
(Continued)

(52) U.S. Cl.
CPC ....... *A61M 39/1011* (2013.01); *A61M 5/14566* (2013.01); *A61M 5/1458* (2013.01);
(Continued)

(58) Field of Classification Search
USPC .......................................... 604/131
See application file for complete search history.

(56) References Cited

U.S. PATENT DOCUMENTS

| 4,636,198 A | 1/1987 | Stade |
| 4,749,109 A | 6/1988 | Kamen |

(Continued)

FOREIGN PATENT DOCUMENTS

| WO | 9910032 A1 | 3/1999 |
| WO | 2006091695 A1 | 8/2006 |
| WO | 2008063529 A1 | 5/2008 |

OTHER PUBLICATIONS

U.S. Patent and Trademark Office, Written Opinion in PCT Application Serial No. PCT/US2010/051800, Apr. 18, 2012.
(Continued)

*Primary Examiner* — Jason Flick
(74) *Attorney, Agent, or Firm* — Wood, Herron & Evans, LLP (57) ABSTRACT

A medical injector (300) includes a medicament container (310), a non-manual actuator (320), and an adapter (340) for coupling the medicament container (310) and the non-manual actuator (320). The adapter (340) includes a proximal end portion (341) configured to engage a drive element (326) of the non-manual actuator (320). The adapter (340) also includes a distal end portion (344) including a surface (345) configured to engage a movable element (319) within the medicament container (310). The adapter (340) may include a coupler (350) having at least one coupling member (353) configured to removably couple the adapter (340) to the medicament container (310), and also having a connector (354) configured to removably couple the adapter (340) to the non-manual actuator (320). The drive element (326) of the non-manual actuator (320) may apply a movement force to the adapter (340), which then pushes the movable element (319) within the medicament container (310) to inject medicament into a patient.

21 Claims, 6 Drawing Sheets

(51) Int. Cl.
*A61M 39/10* (2006.01)
*A61M 5/145* (2006.01)
*A61M 5/14* (2006.01)
*A61M 5/24* (2006.01)

(52) U.S. Cl.
CPC ...... *A61M5/1413* (2013.01); *A61M 2005/2411* (2013.01); *A61M 2005/2488* (2013.01); *A61M 2005/2492* (2013.01); *A61M 2039/1033* (2013.01); *A61M 2039/1077* (2013.01)

(56) References Cited

U.S. PATENT DOCUMENTS

| | | | |
|---|---|---|---|
| 5,383,858 A * | 1/1995 | Reilly et al. | 604/152 |
| 5,618,832 A | 4/1997 | Schmidt et al. | |
| 5,947,929 A * | 9/1999 | Trull | 604/152 |
| 6,048,334 A | 4/2000 | Hirschman et al. | |
| 2002/0165491 A1 | 11/2002 | Reilly | |
| 2009/0036771 A1 | 2/2009 | Fago et al. | |
| 2009/0112087 A1* | 4/2009 | Fago | 600/432 |
| 2009/0124995 A1* | 5/2009 | Bruce | 604/506 |
| 2009/0198183 A1 | 8/2009 | Krumme et al. | |

OTHER PUBLICATIONS

U.S. Patent and Trademark Office, International Preliminary Report on Patentability in PCT Application Serial No. PCT/US2010/051800, Jul. 26, 2012.

U.S. Patent and Trademark Office, International Search Report and Written Opinion in PCT Application Serial No. PCT/US2010/051800, Dec. 9, 2010.

European Patent Office, Supplementary European Search Report in EP Application No. 10822682, Jul. 23, 2014.

\* cited by examiner

MEDICAL INJECTOR AND ADAPTER FOR COUPLING A MEDICAMENT CONTAINER AND AN ACTUATOR

CROSS-REFERENCE TO RELATED APPLICATION

This application claims the priority of U.S. Provisional Patent Application Ser. No. 61/249,380, filed on Oct. 7, 2009, the disclosure of which is incorporated by reference herein.

FIELD OF THE INVENTION

This invention generally relates to medical injectors used for a variety of purposes, and particularly to a medical injector including an adapter for coupling a medicament container and an actuator.

BACKGROUND OF THE INVENTION

Known dermal fillers can be injected into a patient's body to augment soft tissue portions within the body. For example, some known filler compositions can be injected adjacent the urinary sphincter muscle to increase the volume of the tissue within the urinary tract to treat urinary incontinence. Known dermal fillers can also be injected into the skin to change the contour of and/or increase the volume of the skin. For example, known high viscosity compositions can be injected within facial skin to remove wrinkles, treat scars, or the like.

Some known procedures for injecting dermal fillers into a patient include injecting the dermal filler using a standard medical syringe. In such conventional medical syringes, a practitioner applies manual pressure to a plunger to force dermal filler from the syringe body. However, the force applied manually by a practitioner can be sporadic, leading to injection of more or less dermal filler at a particular location than desirable. In this regard, manual force may be insufficient to provide the desired flow rate of dermal filler into the patient. Practitioners may also develop user fatigue and/or chronic health problems such as arthritis by continuously applying enough manual force to actuate injection of the dermal filler.

Therefore, non-manual actuators have been developed for use with medical syringes as part of a medical injector, to avoid the aforementioned problems with manual actuation of a medical syringe. However, these non-manual actuators are currently specially designed for a corresponding or particular medical syringe. Consequently, the non-manual actuator must be replaced any time a different type of medical syringe is to be used to inject dermal filler or other liquids into a patient. Furthermore, the non-manual actuator may not maintain a fluid-tight connection with a medical syringe, which may lead to leaking of material from the syringe during actuation.

Thus, it would be desirable to provide an improved medical injector and an adapter that address at least some of these problems with conventional injection systems and syringes.

SUMMARY

According to one embodiment, a medical injector includes a medicament container configured to be coupled to a needle and contain a medicament. The medicament container includes a movable element adapted to push the medicament through the medicament container. The medical injector also includes a non-manual actuator including a drive element configured to apply a movement force. The medical injector further includes an adapter coupled to the medicament container and the non-manual actuator. The adapter includes a proximal end portion configured to engage the drive element, and a distal end portion coupled to the proximal end portion. The distal end portion includes a surface configured to engage the movable element and defines an outer diameter sized to slide within the medicament container. When the drive element applies a movement force to the proximal end portion of the adapter, the distal end portion of the adapter slides within the medicament container and pushes the movable element, which pushes the medicament through the medicament container to inject the medicament into a patient.

According to another embodiment, an adapter for coupling a medicament container and a non-manual actuator includes a proximal end portion and a distal end portion. The proximal end portion is configured to engage a drive element of the non-manual actuator. The distal end portion is coupled to the proximal end portion and includes a surface configured to engage a movable element of the medicament container. The distal end portion also defines an outer diameter sized to slide within the medicament container. The adapter may also include a coupler including a protrusion defining a lumen for receiving the proximal end portion or the distal end portion. The coupler further includes at least one coupling member configured to removably couple the adapter to the medicament container, and a connector configured to removably couple the adapter to the non-manual actuator.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the invention.

DETAILED DESCRIPTION

As used herein, the words "proximal" and "distal" refer to direction closer to and away from, respectively, an operator (e.g., surgeon, physician, nurse, technician, etc.) of the medical device. Thus, for example, the end of the medicament delivery device contacting the patient's body would be the distal end of the medicament delivery device, while the end opposite the distal end would be the proximal end of the medicament delivery device.

As used herein, the words "non-manual" or "non-manually" are used to describe an operation and/or an apparatus in which a source of energy and/or a force for carrying out the operation and/or a function of the apparatus is not directly produced by a human. For example, an apparatus for non-manually injecting a dermal filler can include any apparatus in which the force to inject the dermal filler is not directly produced by a human. Examples of a non-manual injection apparatus include an apparatus having a compressed gas source to provide the injection force, an apparatus having a spring to provide the injection force, and an apparatus having an electric motor to provide the injection force. An apparatus for non-manually injecting a dermal filler, however, can include a manual actuator (e.g., an on/off switch, a push button, a foot pedal or the like) to initiate the non-manual injection.

Medical injectors and methods of injecting dermal fillers are described herein. In some embodiments, an apparatus includes an adapter having a first portion and a second portion. The first portion of the adapter is configured to be coupled to a non-manual actuator. The second portion of the adapter is configured to be disposed within a medicament container, such as, for example a syringe. The adapter is configured to transfer a kinetic energy produced by the actuator to a medicament within the medicament container such that the medicament can be injected from the medicament container.

Figure 1:
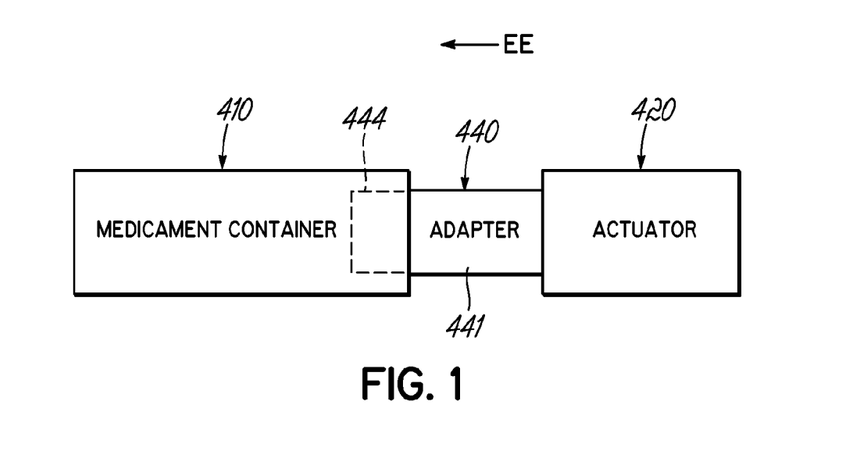
FIG. 1 is a schematic illustration of an adapter according to one embodiment of the invention.

FIG. 1 is a schematic illustration of an adapter 440 according to an embodiment. The adapter 440 includes a first portion 444 and a second portion 441. The first portion 444 of the adapter 440 is disposed within a medicament container 410. In some embodiments, the first portion 444 of the adapter 440 can contact a portion of a plunger (not shown) moveably disposed within the medicament container 410. In other embodiments, at least the first portion 444 of the adapter 440 is coupled to a portion of a plunger moveably disposed within the medicament container 410. In yet other embodiments, the first portion 444 can be disposed within the medicament container 410 and in direct contact with a medicament (not shown in FIG. 1) contained therein.

The second portion 441 of the adapter 440 is coupled to an actuator 420. The actuator 420 can be any suitable energy source and/or actuator that produce a kinetic energy to move a medicament (not shown in FIG. 1) within the medicament container. In some embodiments, the actuator 420 can include a source of compressed gas. In other embodiments, the actuator 420 can include a drive shaft configured to be moved by an electric motor. In some embodiments, the second portion 441 of the adapter 440 is configured to be moveably disposed within the medicament container 410. For example, in some embodiments, a portion of the medicament container 410 can be coupled to a portion of the actuator 420 such that the adapter 440 is substantially disposed within the medicament container 410.

The adapter 440 is configured to transfer a kinetic energy produced by the actuator 420 to a medicament within the medicament container such that the medicament can be injected from the medicament container. For example, in some embodiments, the adapter 440 can move a plunger (not shown) within the medicament container 410 to inject medicament from the medicament container. Specifically, actuator 420 can produce a force acting on the second portion 441 of the adapter 440, thereby causing the adapter 440 to move in a first direction, as indicated by arrow EE. In this manner, the adapter 440 can move the plunger in the direction EE within the medicament container 410. In other embodiments, the adapter 440 can directly contact and/or move the medicament within the medicament container.

In some embodiments, the adapter 440 can be configured to store a portion of the kinetic energy produced by the actuator 420. For example, in some embodiments, the adapter 440 can include a compressible material (e.g., an internal surface containing a gas) such that the adapter 440 can store at least a portion of the kinetic energy produced by the actuator 420. In this manner, when the actuator 420 produces a first force, the adapter can transfer a second force different than the first force to the medicament.

The adapter 440 and the actuator 420 can be coupled together by any suitable means. For example, the adapter 440 and the actuator 420 can be coupled together by a mechanical coupling (e.g., an interference fit, detents, a threaded coupling, or the like), an electronic coupling (e.g., a magnetic coupling), a chemical bond, a hydraulic coupling and/or a pneumatic coupling (e.g., a vacuum coupling).

Figure 2:
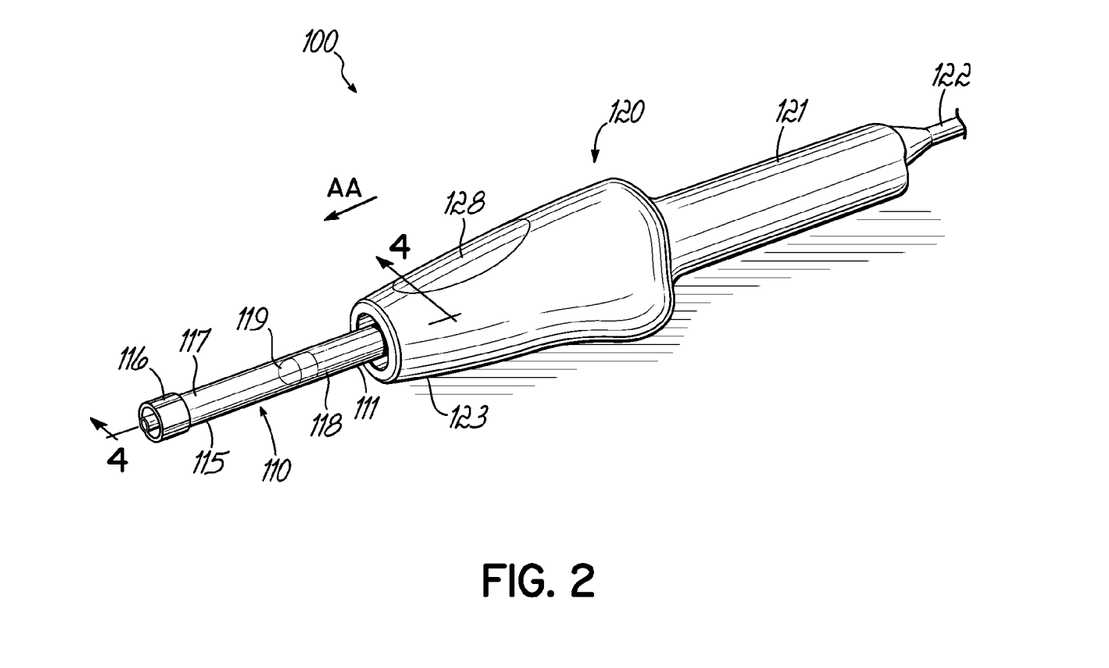
FIG. 2 is a perspective view of a medical injector according to one embodiment of the invention.
Figure 5:
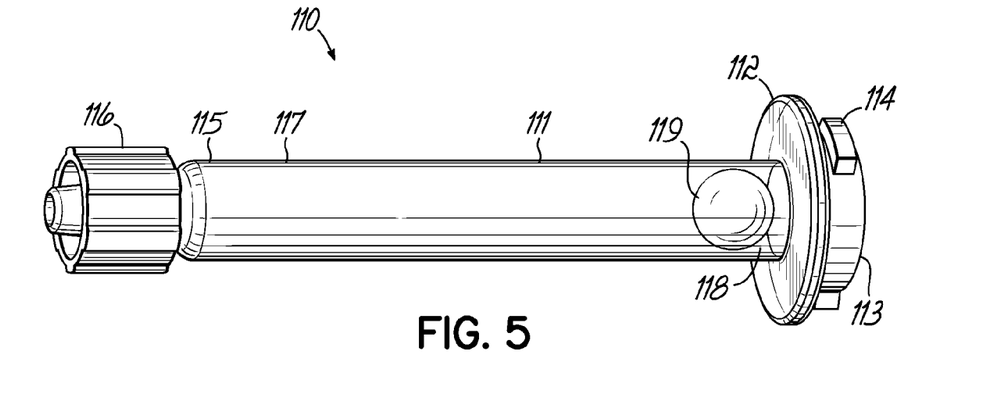
FIG. 5 is a perspective view of a medicament container of the medical injector shown in FIG. 2.

FIG. 2 is a perspective view of a medical injector 100 according to an embodiment. The medical injector 100 includes a medicament container 110, an actuator 120, and an adapter 140. The medicament container 110 has a proximal end portion 111 and a distal end portion 115. The medicament container 110 includes a spherical plunger 119 moveably disposed therein such that the medicament container 110 is divided into a first portion 117 distal to the spherical plunger 119 and a second portion 118 proximate to the spherical plunger 119. The first portion 117 of the medicament container 110 is configured to contain a medicament. The medicament can be any medicament suitable for being injected into a body, such as, for example a dermal filler. The proximal end portion 111 of the medicament container 110 includes a flange 112 and a connector 113 with locking tabs 114 (see FIGS. 3 and 5). The connector 113 extends from the flange 112 of the medicament container 110 and is configured to couple the medicament container 110 to the actuator 120, as described herein.

A coupler 116 is disposed at the distal end portion 115 of the medicament container 110. The coupler 116 is configured to removably couple a needle (not shown in FIG. 2) to the distal end portion 115 of the medicament container 110 such that the needle is in fluid communication with the first portion 117 of the medicament container 110. The coupler 116 can include or take a form of any suitable coupling mechanism configured to produce a substantially fluid-tight coupling between the needle and the medicament container 110. For example, in some embodiments, the coupler 116 can be a Luer lock fitting that threadedly engages a hub of the needle and maintains the hub in position about a protrusion (not shown in FIG. 2) at the distal end portion 115 of the medicament container 110. In such an arrangement, the protrusion and the needle hub can have mating tapered surfaces such that a substantially fluid-tight interface is produced when the needle hub is coupled to the medicament container 110 by the coupler 116.

The actuator 120 is a non-manual actuator configured to be removably coupled to the medicament container 110 and to non-manually move the spherical plunger 119 within the medicament container 110. The actuator 120 can be, for example, a Midwest Comfort Control™ Syringe manufactured by Dentsply Professional, a division of Dentsply International. Such an example is illustrated in Patent Publication No. 2005/0101913, filed Dec. 17, 2004, which is incorporated herein by reference in its entirety. The actuator 120 includes an electric motor (not shown in FIGS. 2-7), a drive shaft 126 configured to be driven by the electric motor, and a push button 128 configured to control the operation of the electric motor. The actuator 120 includes a distal end portion 123 and a proximal end portion 121. The distal end portion 123 of the actuator 120 is coupled to the medicament container 110 via a coupling portion 124 of the actuator 120 (see e.g., FIG. 3). Specifically, the coupling portion 124 of the actuator 120 is configured to receive the connector 113 of the medicament container 110 such that the actuator 120 and the medicament container 110 can be removably coupled together (see FIG. 4). Moreover, when the medicament container 110 is coupled to the actuator 120, the flanged portion 112 of the medicament container 110 abuts the actuator 120 such that a substantially fluid-tight seal is produced between the medicament container 110 and the actuator 120.

Figure 3:
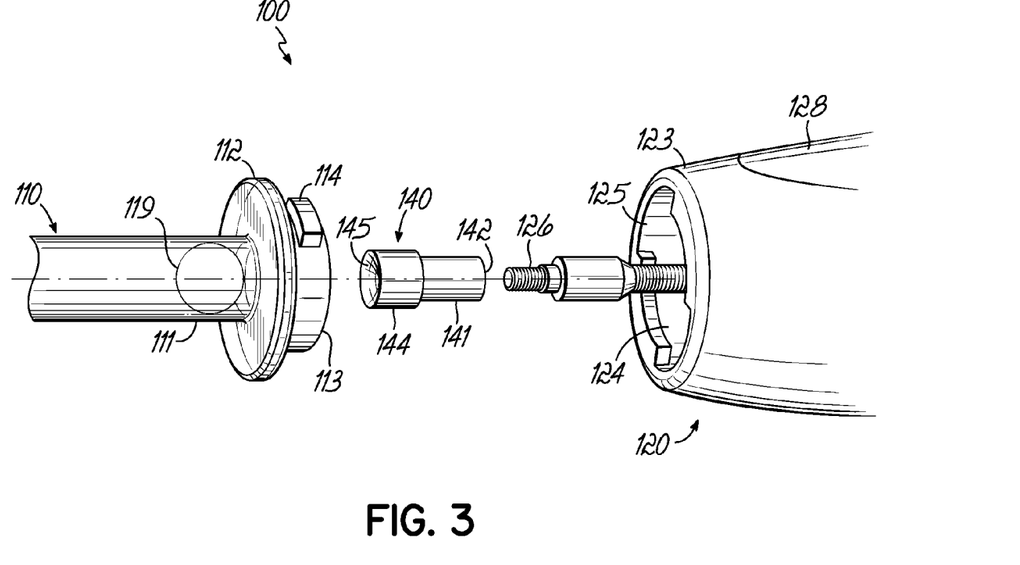
FIG. 3 is an exploded view of the medical injector shown in FIG. 2.
Figure 4:
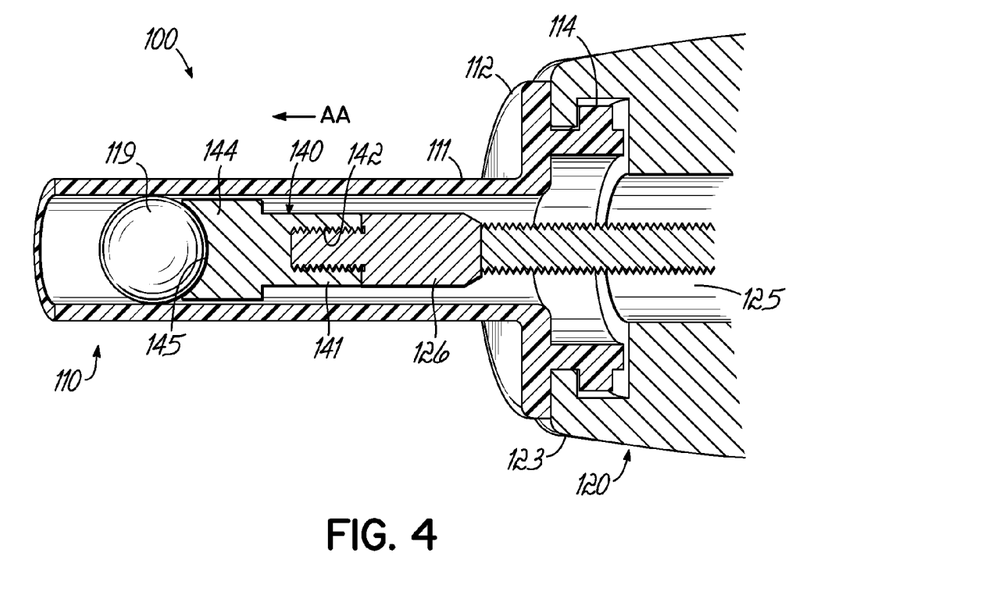
FIG. 4 is a cross-sectional view of the medical injector shown in FIG. 2 taken along the line 4-4 in FIG. 2.

As shown in FIG. 3, which is an exploded view of a portion of the medical injector 100, the actuator 120 defines a lumen 125 within which the drive shaft 126 is disposed. The drive shaft 126 is movable within the lumen 125 such that a distal end of the drive shaft 126 can extend from the distal end portion 123 of the actuator 120 and into the second portion 118 of the medicament container 110 when the medicament container 110 is coupled to the actuator 120, as shown in FIGS. 2 and 4. In this manner, as described in more detail herein, the drive shaft 126 can move the spherical plunger 119 within the medicament container 110 to inject the medicament. The outer surface of the drive shaft 126 includes male threads such that the drive shaft 126 can be threadedly coupled to the adapter 140, as described herein.

The drive shaft 126 is operatively coupled to the electric motor (not shown) such that the electric motor can move the drive shaft 126 within the lumen 125. In some embodiments, for example, the drive shaft can be operatively coupled to the electric motor via a screw drive. With such an arrangement, rotational motion of the electric motor can result in rotational motion of the drive shaft 126, which can in turn result in longitudinal movement of the drive shaft 126. The proximal end portion 121 of the actuator 120 includes a connection portion 122 (e.g., a power cord) configured to provide electric power to the actuator 120. The electric motor can be any suitable electric device configured to move the drive shaft 126. In some embodiments, the electric motor can be an electrically-powered stepper motor. In other embodiments, the electric motor can be of any conventional design that facilitates the longitudinal displacement of the drive shaft 126.

The electric motor is controlled by the push button 128 disposed on the outer surface of the actuator 120. Said another way, the push button 128 regulates the electric motor of the actuator 120 to control movement of the drive shaft 126. More particularly, the push button 128 can control the starting and stopping of the drive shaft 126, as well as the amount of and speed of the longitudinal displacement of the drive shaft 126. In this manner, a user can actuate the actuator 120 via the push button 128 to initiate the non-manual injection of the dermal filler from the medicament container 110 through the needle. As described above, because the dermal filler is conveyed from the medicament container 110 non-manually, the user is not burdened with producing the energy and/or force necessary to cause the dermal filler to be conveyed at the desired flow rate. This arrangement can result in a repeatable, continuous and/or controlled injection of the medicament (e.g., dermal filler).

Figure 6:
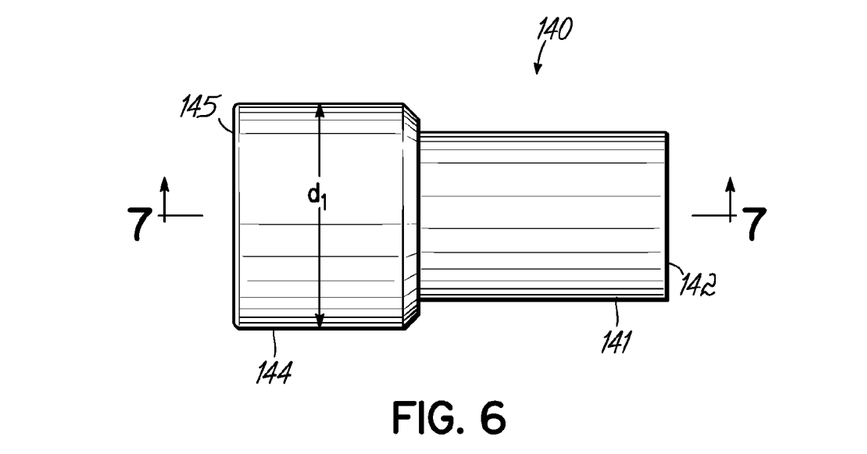
FIG. 6 is a side view of an adapter of the medical injector shown in FIG. 2.
Figure 7:
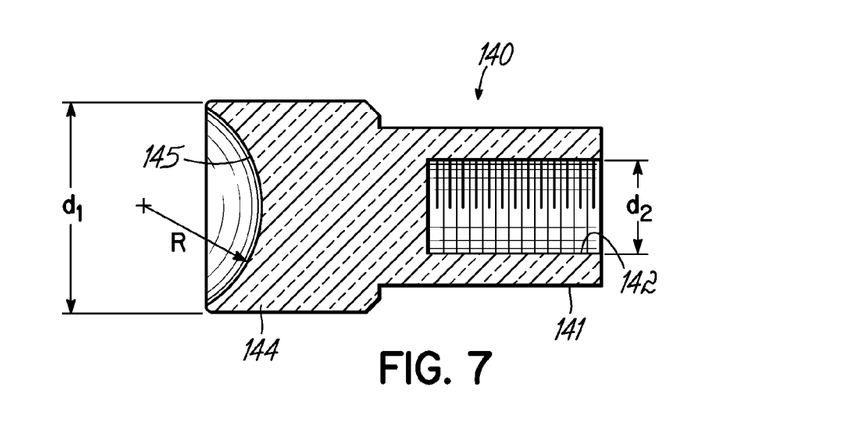
FIG. 7 is a cross-sectional view of the adapter shown in FIG. 6 taken along the line 7-7 in FIG. 6.

The adapter 140 includes a distal end portion 144 and a proximal end portion 141. The adapter 140 is configured to be coupled to the drive shaft 126. As shown in FIGS. 6 and 7, the largest portion of the adapter 140 has an outer diameter d1 such that the adapter 140 can be moveably disposed within the medicament container 110 without engaging a sidewall of the medicament container 110 (see FIG. 4). More specifically, the adapter 140 moves within the medicament container 110 such that no friction is produced between the adapter 140 and the medicament container 110. In some embodiments, for example, the outer diameter d1 can be approximately 0.230 inches.

The proximal end portion 141 of the adapter 140 includes a bore 142 that receives a distal end of the drive shaft 126 of the actuator 120. As shown in FIG. 7, the bore 142 has an inner diameter d2, that can be, for example, approximately 0.070 inches. A portion of the bore 142 of the adapter 140 includes female threads (not shown) configured to receive the male threads of the drive shaft 126 to threadedly couple the adapter 140 to the actuator 120. In this manner, the adapter 140 moves with the drive shaft 126 of the actuator 120 such that the adapter 140 is longitudinally displaced within the medicament container 110 when the drive shaft 126 is moved by the electric motor of the actuator 120. In other embodiments, however, the adapter 140 and the drive shaft 126 can be coupled by any suitable means. For example, the coupling can be a mechanical coupling (e.g., an interference fit, detents, a threaded coupling, or the like), an electro-magnetic coupling (e.g., a magnetic coupling), a chemical bond, a hydraulic coupling and/or a pneumatic coupling (e.g., a vacuum coupling).

The distal end portion 144 of the adapter 140 is configured to contact the plunger 119 of the medicament container 110 such that the plunger 119 moves within the medicament container 110 when the drive shaft 126 and/or the adapter 140 move longitudinally. Said another way, the adapter 140 is configured to move the plunger 119 of the medicament container 110 via the drive shaft 126 of the actuator 120. As shown in FIG. 4, the adapter 140 includes a curved distal end surface 145 within which at least a portion of the spherical plunger 119 of the medicament container 110 can be disposed. Said another way, the distal end surface 145 of the adapter 140 has a radius of curvature R that is substantially the same as a radius of the spherical plunger 119 of the medicament container 110, as shown in FIG. 7. In some embodiments, the radius of curvature R is approximately 0.125 inches.

In use, a user actuates the medical injector 100 by pressing the push button 128 disposed on the outer surface of the actuator 120. The push button 128 activates the electric motor such that the electric motor moves the drive shaft 126 of the actuator 120 in the direction AA. As a result, the adapter 140 moves the plunger 119 within the medicament container 110 in the direction AA. In this manner, the medicament, such as, for example, a dermal filler, is conveyed in direction AA from the medicament container 110 to a patient through the needle (not shown).

Figure 8:
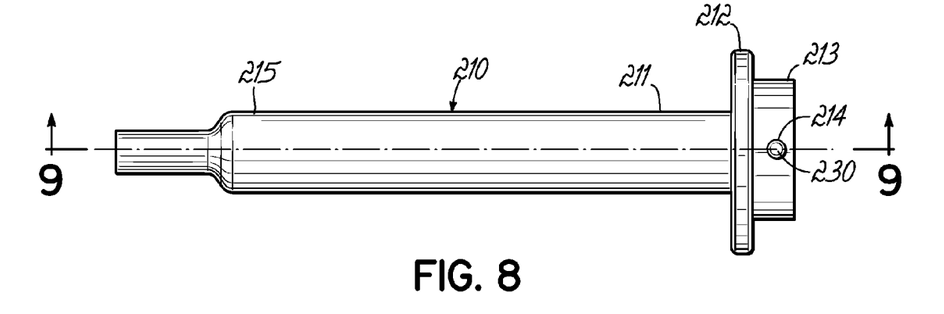
FIG. 8 is a side view of a medicament container according to another embodiment of the invention.
Figure 9:
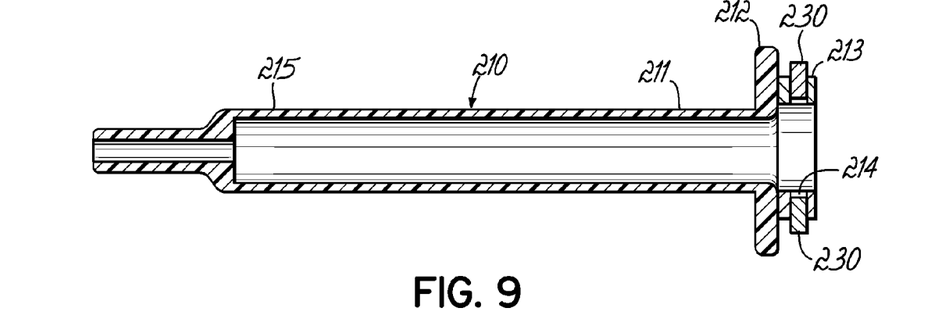
FIG. 9 is a cross-sectional view of the medicament container shown in FIG. 8 taken along the line 9-9 in FIG. 8.

In some embodiments, a medical injector can include a medicament container with locking pins configured to removably couple the medicament container to an actuator. For example, FIG. 8 is a side view and FIG. 9 is a cross-sectional view of a medicament container 210 with locking pins 230. The medicament container 210 includes a proximal end portion 211 and a distal end portion 215. A coupler (not shown) is configured to be disposed on the distal end portion 215 of the medicament container 210, as described above. The proximal end portion 211 of the medicament container 210 includes a flange 212 and a coupling portion 213 defining two openings 214. The coupling portion 213 extends from the flange 212 of the medicament container 210 and is configured to couple the medicament container 210 to an actuator (not shown), as described herein.

As shown in FIG. 9, the openings 214 of the medicament container 210 are configured to receive locking pins 230. The locking pins 230, which can be, for example, substantially rigid and cylindrically shaped, form an interference fit with the openings 214 of the coupling portion 213 such that the locking pins 230 are fixedly coupled to the coupling portion 213 of the medicament container 210. The locking pins 230 are configured to removably couple the medicament container 210 to an actuator (see e.g., actuator 120 shown and described above). More specifically, the locking pins 230 can be disposed within a keyed recess of a coupling portion of the actuator (see e.g., coupling portion 124 shown and described above) when the locking pins 230 are coupled to the medicament container 210. The medicament container 210 can then be rotated about its longitudinal axis to couple the locking pins 230 within the keyed recess such that the medicament container 210 is removably coupled to the actuator (not shown). In this manner, the locking pins 230 function similar to the locking tabs 114 described above.

While the medicament container 210 is described above as including locking pins 230 to couple the medicament container 210 to the actuator (not shown), in some embodiments, the actuator includes locking pins such that the locking pins of the actuator couple the medicament container 210 to the actuator.

Figure 10:
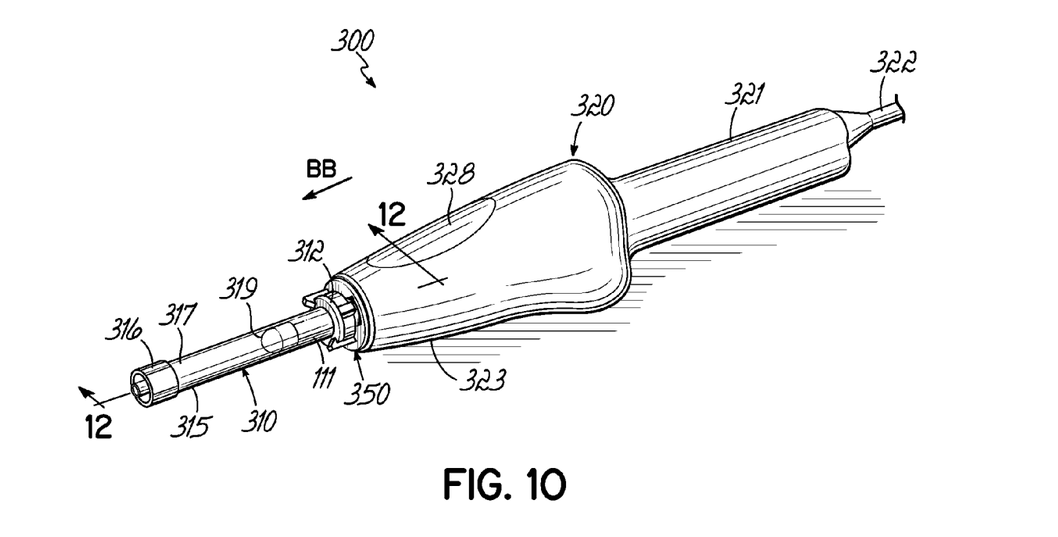
FIG. 10 is perspective view of a medical injector according to another embodiment of the invention.

FIG. 10 is a perspective view of a medical injector 300 according to another embodiment. The medical injector 300 includes a medicament container 310, an actuator 320, and an adapter assembly 360. The medicament container 310, which is a commercially-available syringe, such as, for example, a Safey-Lok™ syringe manufactured by Becton Dickenson, has a proximal end portion 311 and a distal end portion 315. The medicament container 310 includes a piston 319 moveably disposed therein such that the medicament container 310 is divided into a first portion 317 distal to the piston 319 and a second portion 318 proximate to the piston 319. The first portion 317 of the medicament container 310 is configured to contain a medicament. The medicament can be any medicament suitable for being injected into a body, such as, for example, a dermal filler. A coupler 316 is disposed at the distal end portion 315 of the medicament container 310. As described above, the coupler 316 is configured to removably couple a needle (not shown in FIG. 10) to the distal end portion 315 of the medicament container 310.

Figure 11:
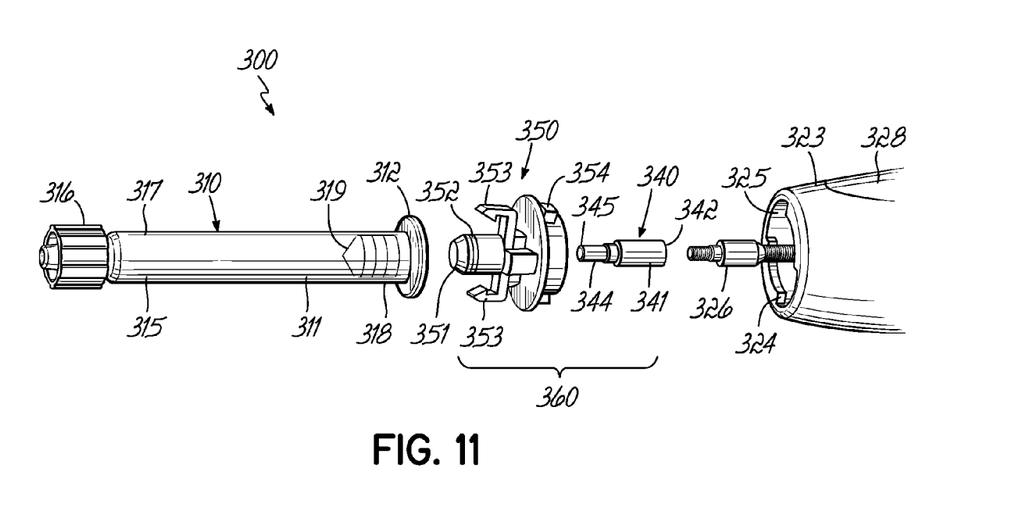
FIG. 11 is an exploded view of the medical injector shown in FIG. 10.
Figure 12:
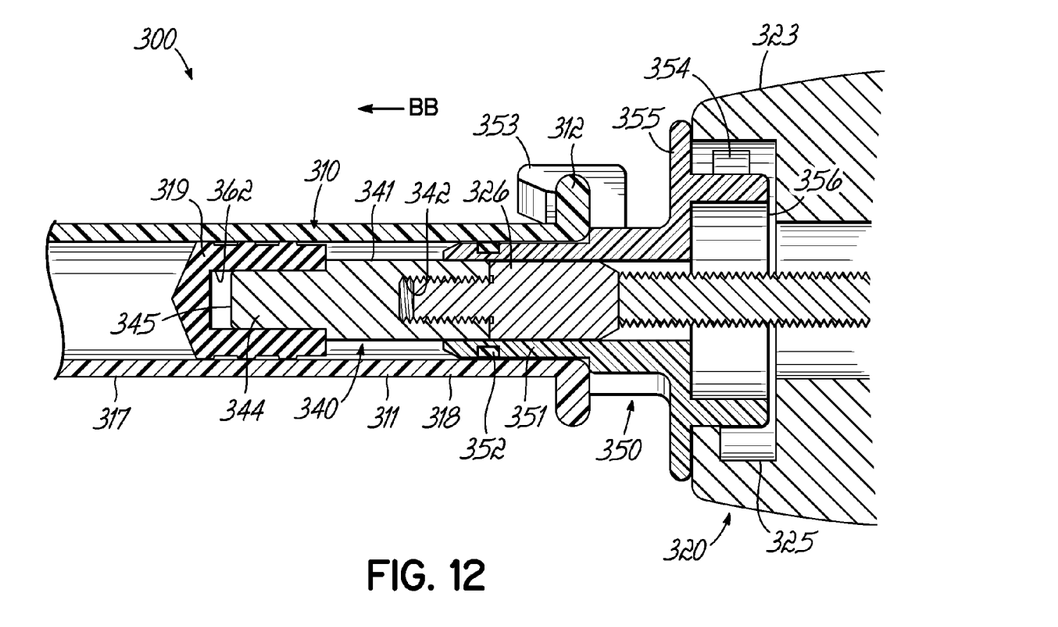
FIG. 12 is a cross-sectional view of the medical injector shown in FIG. 10 taken along the line 12-12 in FIG. 10.

The actuator 320 is a non-manual actuator configured to be removably coupled to the medicament container 310 and to non-manually move the piston 319 within the medicament container 310. The actuator 320, which is similar to the actuator 120 shown and described above, includes a distal end portion 323 and a proximal end portion 321. The distal end portion 323 of the actuator 320 is coupled to the medicament container 310 via a coupler 350 of the adapter assembly 360, as described herein. As shown in FIG. 11, which is an exploded view of the medical injector 300, the actuator 320 defines a lumen 325 within which a drive shaft 326 is disposed. The drive shaft 326 is movable within the lumen 325 such that a distal end of the drive shaft 326 can extend from the distal end portion 323 of the actuator 320 and into the second portion 318 of the medicament container 310 when the medicament container 310 is coupled to the actuator 320, as shown in FIGS. 10 and 12. In this manner, as described above, the drive shaft 326 can move the piston 319 within the medicament container 310 to inject the medicament. The outer surface of the drive shaft 326 includes male threads such that the drive shaft 326 can be threadedly coupled to the adapter 340, as described herein.

The proximal end portion 321 of the actuator 320 includes a connection portion 322 configured to electric provide power to an electric motor (not shown) associated with the actuator 120. The electric motor is controlled by the push button 328 disposed on the outer surface of the actuator 320. More particularly, the push button 328 regulates the electric motor of the actuator 320 to control movement of the drive shaft 326, as described above.

The adapter assembly 360 is configured to couple the medicament container 310 to the actuator 320. In this manner, an off-the-shelf syringe (e.g., the medicament container 310) can be coupled to the actuator 320. The adapter assembly 360 includes a coupler 350 and an adapter 340. The adapter 340 includes a distal end portion 344 and a proximal end portion 341. The adapter 340 is configured to be coupled to the drive shaft 326. As shown in FIG. 12, the largest portion of the adapter 340 has a diameter such that the adapter 340 can be moveably disposed within the medicament container 310 without engaging a sidewall of the medicament container 310, as described above. Also described above, the proximal end portion 341 of the adapter 340 includes a bore 342 that receives a distal end of the drive shaft 326 of the actuator 320. A portion of the bore 342 of the adapter 340 includes female threads (not shown) configured to receive the male threads of the drive shaft 326 to threadedly couple the adapter 340 to the actuator 320, as described above. In this manner, the adapter 340 moves with the drive shaft 326 of the actuator 320 such that the adapter 340 is longitudinally displaced within the medicament container 310 when the drive shaft 326 is moved by the electric motor of the actuator 320.

The distal end portion 344 of the adapter 340 is configured to fit within a bore 362 of the piston 319 of the medicament container 310. To this end, the bore 362 of the piston 319 of the medicament container 310 receives the distal end portion 344 of the adapter 340 such that an end surface 345 of the adapter 340 is coupled to the piston 319. In this manner, the piston 319 is can be moved within the medicament container 310 via the adapter 340. Said another way, the adapter 340 is configured to move the piston 319 within the medicament container 310 when the drive shaft 326 of the actuator 320 moves within the medicament container 310. In some embodiments, the bore 362 of the piston 319 and the distal end portion 344 of the adapter 340 form an interference fit. In some embodiments, however, the adapter 340 and the piston 319 can be coupled by any suitable means. For example, the coupling can be a mechanical coupling (e.g., an interference fit, detents, a threaded coupling, or the like), an electro-magnetic coupling (e.g., a magnetic coupling), a chemical bond, a hydraulic coupling and/or a pneumatic coupling (e.g., a vacuum coupling).

The coupler 350 of the adapter assembly 360 is configured to removably couple the actuator 320 to the medicament container 310. More particularly, the coupler 350 of the adapter assembly 360 is configured to couple the actuator 320 to a standard, commercially-available syringe. In this manner, the actuator 320 can be used on a variety of different medicament containers 310 without the need to modify the actuator 320 and/or the medicament container 310.

Figure 13:
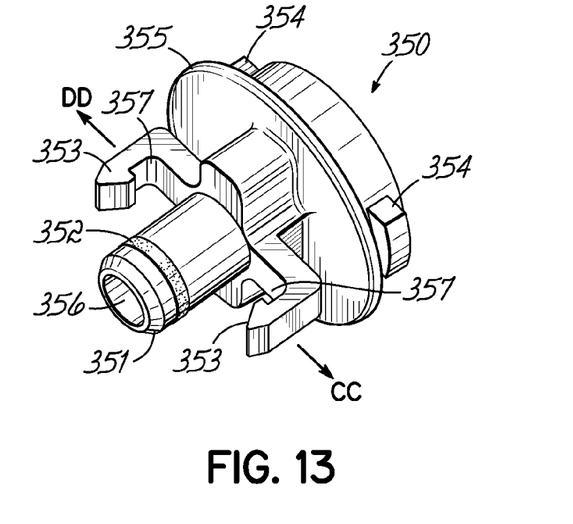
FIG. 13 is a perspective view of a coupler of the medical injector shown in FIG. 10.

As shown in FIG. 13, the coupler 350 includes a protrusion 351, a sealing member 352, two coupling members 353, a flange 355 and a key connector 354. The protrusion 351 is configured to be disposed within the second portion 318 of the medicament container 310 when the coupler 350 is coupled to the medicament container 310. The sealing member 352 is disposed about the protrusion 351 and forms a substantially fluid-tight seal between the protrusion 351 and the inner surface of the medicament container 310 when the coupler 350 is coupled to the medicament container 310. The sealing member 352 can be, for example, an o-ring, and can be constructed from any suitable material that is compatible with the medicament.

The coupling members 353 are disposed approximately equidistance circumferentially about the coupler 350. Said another way, the coupling members 353 are disposed approximately 180 degrees apart. In this manner the coupling members 353 engage a flange 312 of the medicament container 310 at two distinct circumferential locations when the coupler 350 is coupled to the medicament container 310. As shown in FIG. 13, each coupling member 353 defines a channel 357 within which the flange 312 of the medicament container 310 is received when the coupler 350 is coupled to the medicament container 310. More particularly, each coupling member 353 is configured to bend outwardly, as shown by arrows CC and DD, when pressed against the flange 312 to allow the flange 312 to be disposed within the channel 357. When the flange 312 of the medicament container 310 is disposed within the channel 357, the coupling members 353 move back to their respective relaxed positions such that the flange 312 of the medicament container 310 and the coupling members 353 cooperatively limit the axial movement of the medicament container 310 relative to the actuator 320.

The coupler 350 is coupled to the actuator 320 via the connector 354 of the coupler 350. Specifically, the coupling portion 324 of the actuator 320 is configured to fit the connector 354 of the coupler 350 such that the actuator 320 is removably coupled to the coupler 350 (see FIG. 12). In this manner, the medicament container 310 and the actuator 320 are collectively coupled via the coupler 350. As a result, the flange 355 of the coupler 350 abuts the actuator 320 such that a substantially fluid-tight seal is produced between the coupler 350 and the actuator 320. The coupler 350 defines a lumen 356 such that the adapter 340 and/or the drive shaft 326 of the actuator 320 are moveably disposed within the lumen 356 defined by the coupler 350 when the actuator 320 is coupled to the medicament container 310 via the coupler 350.

In use, a user actuates the medical injector 300 by pressing the push button 328 disposed on the outer surface of the actuator 320. The push button 328 activates the electrical drive motor such that the electrical drive motor moves the drive shaft 326 of the actuator 320 in the direction BB. As a result, the adapter 340 moves the plunger 319 within the medicament container 310 in the direction BB. In this manner, the medicament, such as, for example, a dermal filler, is conveyed in direction BB from the medicament container 310 to a patient through the needle (not shown).

While various embodiments of the invention have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

In some embodiments, the medicament container 110, 210 and 310 is configured to contain a medicament (not shown) having a high viscosity (i.e., a medicament having a viscosity of at least 100 Poise). The medicament can be any medicament suitable for being injected into a body. For example, in some embodiments, the medicament can be a high viscosity dermal filler (e.g., a liquid dermal filler, a paste-like dermal filler, a dermal filler including both a liquid component and a solid component, or the like). In some embodiments, the medicament can have a viscosity of at least 1000 Poise (100 N-sec/m2). In other embodiments, the medicament can have a viscosity of at least 10,000 Poise. In yet other embodiments, the medicament can have a viscosity of at least 100,000 Poise.

The medicaments and/or dermal fillers described above can be any material suitable for augmenting soft tissue. In some embodiments, a medicament and/or dermal filler can include a pain reliever, such as, for example, lidocaine. In other embodiments, a medicament and/or dermal filler can include a colorant and/or a marker. For example, in some embodiments a medicament and/or dermal filler can include a radio-opaque marker. In other embodiments, a medicament and/or dermal filler can include a tattoo ink.

In some embodiments, a dermal filler can include, for example, a side chain crystalline (SCC) polymer of the type disclosed in International Patent Application No. PCT/US2007/023226, entitled "Compositions, Devices and Methods for Modifying Soft Tissue," which is incorporated herein by reference in its entirety. In other embodiments, a dermal filler can include hyaluronic acid. In yet other embodiments, a dermal filler can include polyacrylamide, collagen (either human and/or bovine), polymethylmethacrylate, silicone, calcium hydroxylapatite (CaHA), hydrophilic polyacrylamid gel (PAAG), and/or poly-L-lactic acid hydrogel (PLLA).

In some embodiments, a dermal filler can include any of the following commercially-available dermal fillers: Puragen™ and its derivatives, produced by Mentor Corporation, Belotero® and its derivatives, produced by Merz Pharmaceuticals, BIO-ALCAMIDT™ and its derivatives, produced by Polymekon S.R.L., Outline® and its derivatives, produced by ProCytech, HylaNew® and its derivatives, produced by Prollenium Medical Technologies, Inc., Restylane® and its derivatives, produced by Q-Med or Medicis Pharmaceutical Corporation, Reviderm USA and its derivatives, produced by Rofil Medical International N.V., Teosyal® and its derivatives, produced by Teoxane Laboratories, Fascian® and its derivatives, produced by Fascia Biosystems, LLC, FG-5017 and its derivatives, produced by Fibrogen, Inc., Amazingel and its derivatives, produced by FuHua High Molecular Matter Company, Ltd., Laresse® Dermal Filler and its derivatives, produced by FzioMed, Inc., Zyderm® and its derivatives, produced by Inamed Corporation, Isolagen® and its derivatives, produced by Isolagen, Inc., MacDermol® and its derivatives, produced by Laboratories ORGéV, Juvéderm™ and its derivatives, produced by L.E.A. Derm, Hyaluderm® and its derivatives, produced by LCA Pharmaceutical, Silikon® 1000 and its derivatives, produced by Alcon, Inc., Esthèlis and its derivatives, produced by Antesis® S.A., Artefill® and its derivatives, produced by Artes Medical, Inc., Radiesse® and its derivatives, produced by BioForm Medical, Inc., Matridex® and its derivatives, produced by BioPolymer GmbH & Co. KG, Evolence® and its derivatives, produced by ColBar LifeScience Ltd., Aquamid® and its derivatives, produced by Contura International A/S, SurgiDerm® and its derivatives, produced by Labortoire Corneal® Development, Rhegecoll and its derivatives, produced by Dermabiol Institute of Kuhra Vital GmbH, DermaLive® and its derivatives, produced by Derma Tech, and/or Sculptra™ and its derivatives, produced by Dermik® Laboratories.

Although the coupling members 353 are shown and described as being configured to bend outwardly when the coupler 350 is being coupled to the medicament container 310, in other embodiments, the coupling members 353 can be substantially rigid. For example, in some embodiments, the flange 312 of the medicament container 310 does not extend circumferentially around the medicament container 310, but rather two flanges can be positioned on opposite sides of the medicament container 310. In such embodiments, the medicament container 310 can be rotated relative to the coupler 350 until the flanges are out of alignment with the coupling members 353. The coupler 350 can then be disposed about the medicament container 310. The medicament container 310 can then be rotated relative to the coupler 350 until the flanges are aligned with the coupling members 353, thereby securing the medicament container 310 within the coupler 350 such that the medicament container 310 is collectively coupled to the actuator 320.

Although the medicament containers 110, 210 and 310 and the actuators 120 and 320 are shown and described above as being coupled together via the coupling portion 124 and 324 of the actuators 120 and 320, respectively, in some embodiments, the medicament containers 110, 210 and 310 and the actuators 120 and 320 can be coupled together by any suitable means. For example, the medicament containers 110, 210 and 310 and the actuators 120 and 320 can be coupled together by a mechanical coupling (e.g., an interference fit, detents, a threaded coupling, or the like), an electronic coupling (e.g., a magnetic coupling), a chemical bond, a hydraulic coupling and/or a pneumatic coupling (e.g., a vacuum coupling).

The actuators 120 and 320 described above can be any suitable non-manual system for producing a kinetic energy and/or for moving the adapters 140 and 340 within the medicament containers 110 and 310, respectively. For example, as described above, the actuators 120 and 320 can be a Midwest Comfort Control™ Syringe actuator.

Although the actuators 120 and 320 are shown and described as being actuated by push buttons 128 and 328, respectively, in other embodiments, the actuators 120 and 320 can be actuated via a foot switch coupled to the outer surface of the actuator 120 and 320. In such embodiments, the user can initiate the injection of the dermal filler in a "hands free" manner, thereby allowing the user to use their hands to control the placement and/or the movement of the needle within the body. The foot switch can be, for example, an electronic switch, a pneumatic switch or the like. In some embodiments, for example, the foot switch can be wirelessly coupled to the actuator 120 and 320.

Although the actuators 120 and 320 are shown and described as moving the drive shafts 126 and 326 in a single direction (i.e., direction AA and BB, respectively), in other embodiments, the actuators 120 and 320 can move the drive shafts 126 and 326 in more than one direction. Said another way, in some embodiments, the actuators 120 and 320 can be multi-directional systems. In some embodiments, for example, the actuator 120 can move the drive shaft 126 in direction AA and then move the drive shaft 126 in the reverse direction (i.e., opposite the direction AA). Similarly stated, a multi-directional actuator can move a drive shaft in a first direction and then move the drive shaft in a second direction, opposite the first direction. In this manner, a medicament container can be detached from the actuator and a new medicament container attached to the actuator such that the actuator can be reused.

In some embodiments, the medicament containers 110, 310 and 410 can be single-use medicament containers. In other embodiments, however, the medicament containers 110, 310 and 410 can be reusable medicament containers. For example, a patient requiring several injections can be injected a first time with a medicament of a single medicament container. The user, such as, for example, a surgeon, can reload the medicament container with additional medicament and inject the patient a second time.

While the present invention has been illustrated by a description of preferred embodiments and while these embodiments have been described in some detail, it is not the intention of the Applicant to restrict or in any way limit the scope of the appended claims to such detail. Additional advantages and modifications will readily appear to those skilled in the art. The various features of the invention may be used alone or in numerous combinations depending on the needs and preferences of the user.

What is claimed is:

1. A medical injector, comprising:
a medicament container configured to be coupled to a needle and contain a medicament, the medicament container including a spherical piston defining a first radius of curvature and dividing the medicament container into a first portion containing the medicament and a second portion, the spherical piston adapted to force the medicament from the medicament container;
a non-manual actuator including a drive element configured to apply a movement force; and
an adapter coupled to the medicament container and the non-manual actuator, the adapter including a proximal end portion configured to engage the drive element and a distal end portion coupled to the proximal end portion and including a spherical surface having a second radius of curvature equal to the first radius of curvature, the spherical surface configured to engage the spherical piston, the distal end portion defining an outer diameter sized to slide within the medicament container,
wherein when the drive element applies a movement force to the proximal end portion of the adapter, the distal end portion of the adapter slides within the medicament container and drives the spherical piston, which thereby forces the medicament from the medicament container to inject the medicament into a patient.

2. The medical injector of claim 1, wherein the medicament container further includes a distal end portion including a coupler for removably engaging a needle hub of a needle, and the medicament container further includes a proximal end portion including a circumferential flange and a connector configured to engage the non-manual actuator.

3. The medical injector of claim 2, wherein the non-manual actuator includes a distal end with a lumen, and wherein the connector on the proximal end portion of the medicament container includes at least one opening configured to receive a locking pin, the locking pin engaging with the lumen to removably couple the medicament container and the non-manual actuator.

4. The medical injector of claim 2, wherein the non-manual actuator includes a distal end with a lumen, and wherein the connector on the proximal end portion of the medicament container includes at least one locking tab configured to engage the lumen to removably couple the medicament container and the non-manual actuator.

5. The medical injector of claim 2, wherein the circumferential flange sealingly abuts the non-manual actuator when the connector is engaged with the non-manual actuator.

6. The medical injector of claim 1, wherein the drive element of the non-manual actuator is a drive shaft, and wherein the proximal end portion of the adapter includes a bore sized to closely receive the drive shaft.

7. The medical injector of claim 6, wherein the drive shaft includes external threads and the bore of the proximal end portion of the adapter includes internal threads configured to engage the external threads of the drive shaft.

8. A medical injector, comprising:
a medicament container configured to be coupled to a needle and contain a medicament, the medicament container including a movable element adapted to force the medicament from the medicament container;

a non-manual actuator including a drive element configured to apply a movement force;

an adapter coupled to the medicament container and the non-manual actuator, the adapter including a proximal end portion configured to engage the drive element and a distal end portion coupled to the proximal end portion and including a surface configured to engage the movable element, the distal end portion defining an outer diameter sized to slide within the medicament container; and a coupler including a protrusion defining a lumen for receiving the proximal end portion or the distal end portion of the adapter, at least one coupling member configured to removably couple the adapter to the medicament container, and a connector configured to removably couple the adapter to the non-manual actuator, wherein when the drive element applies a movement force to the proximal end portion of the adapter, the distal end portion of the adapter slides within the medicament container and drives the movable element, which thereby forces the medicament from the medicament container to inject the medicament into a patient.

9. The medical injector of claim 8, wherein the medicament container includes a proximal end having a circumferential flange, and wherein the at least one coupling member includes two resiliently-flexible coupling members configured to flex outwardly to capture the circumferential flange between the coupling members.

10. The medical injector of claim 8, wherein the medicament container includes a proximal end with at least one peripheral flange, and wherein the at least one coupling member includes two rigid coupling members disposed 180 degrees apart and configured to rotate into locking engagement with the at least one peripheral flange of the medicament container.

11. The medical injector of claim 8, wherein the non-manual actuator includes a lumen and the connector includes a plurality of locking tabs disposed adjacent to a flange on the coupler such that the flange sealingly abuts the non-manual actuator when the locking tabs engage the lumen of the non-manual actuator.

12. The medical injector of claim 8, wherein the protrusion includes a peripheral seal member configured to seal the connection between the adapter and the medicament container when the at least one coupling member couples the adapter to the medicament container.

13. The medical injector of claim 8, wherein the piston includes a piston bore facing the second portion of the medicament container, and wherein the distal end portion of the adapter is sized to be closely received within the piston bore.

14. The medical injector of claim 8, wherein the drive element of the non-manual actuator is a drive shaft, and wherein the proximal end portion of the adapter includes a bore sized to closely receive the drive shaft.

15. The medical injector of claim 14, wherein the drive shaft includes external threads and the bore of the proximal end portion of the adapter includes internal threads configured to engage the external threads of the drive shaft.

16. An adapter assembly for coupling a medicament container and a non-manual actuator, the medicament container including a movable element adapted to force a medicament from the medicament container, and the non-manual actuator including a drive element adapted to apply a movement force, the adapter assembly comprising:

an adapter further comprising:

a proximal end portion configured to engage the drive element of the non-manual actuator; and a distal end portion coupled to the proximal end portion and including a surface configured to engage the movable element of the medicament container, the distal end portion defining an outer diameter sized to slide within the medicament container; and a coupler including a protrusion defining a lumen for receiving the proximal end portion or the distal end portion, at least one coupling member configured to removably couple the adapter to the medicament container, and a connector configured to removably couple the adapter to the non-manual actuator, wherein when the drive element applies a movement force to the proximal end portion, the distal end portion slides within the medicament container and drives the movable element, which thereby forces the medicament from the medicament container.

17. The adapter assembly of claim 16, wherein the medicament container includes a proximal end having a circumferential flange, and wherein the at least one coupling member includes two resiliently-flexible coupling members configured to flex outwardly to capture the circumferential flange between the coupling members.

18. The adapter assembly of claim 16, wherein the medicament container includes a proximal end with at least one peripheral flange, and wherein the at least one coupling member includes two rigid coupling members disposed 180 degrees apart and configured to rotate into locking engagement with the at least one peripheral flange of the medicament container.

19. The adapter assembly of claim 16, wherein the non-manual actuator includes a lumen and the connector includes a plurality of locking tabs disposed adjacent to a flange on the coupler such that the flange is configured to sealingly abut the non-manual actuator when the locking tabs engage the lumen of the non-manual actuator.

20. An adapter for coupling a medicament container and a non-manual actuator, the medicament container including a spherical piston defining a first radius of curvature and adapted to force a medicament from the medicament container, and the non-manual actuator including a drive element adapted to apply a movement force, the adapter comprising:

a proximal end portion configured to engage the drive element of the non-manual actuator; and a distal end portion coupled to the proximal end portion and including a spherical surface having a second radius of curvature equal to the first radius of curvature, the spherical surface configured to engage the spherical piston of the medicament container, the distal end portion defining an outer diameter sized to slide within the medicament container, wherein when the drive element applies a movement force to the proximal end portion, the distal end portion slides within the medicament container and drives the spherical piston, which thereby forces the medicament from the medicament container.

21. The adapter of claim 20, wherein the drive element of the non-manual actuator includes a drive shaft having external threads, and wherein the proximal end portion includes a bore sized to closely receive the drive shaft and including internal threads configured to engage the external threads of the drive shaft.

* * * * *